(12) United States Patent
Burrells et al.

(10) Patent No.: US 6,987,095 B1
(45) Date of Patent: Jan. 17, 2006

(54) FISH FEED WITH INCREASED NUCLEOTIDE CONTENT

(75) Inventors: Charles Burrells, Midlothian (GB); Paul David Williams, Perth & Kinross (GB)

(73) Assignee: Ewos Limited, Livingston (GB)

( * ) Notice: Subject to any disclaimer, the term of this patent is extended or adjusted under 35 U.S.C. 154(b) by 183 days.

(21) Appl. No.: 10/110,842

(22) PCT Filed: Oct. 11, 2000

(86) PCT No.: PCT/GB00/03899

§ 371 (c)(1),
(2), (4) Date: Aug. 6, 2002

(87) PCT Pub. No.: WO01/26481

PCT Pub. Date: Apr. 19, 2001

(30) Foreign Application Priority Data

Oct. 13, 1999 (GB) .................................. 9924096
Apr. 25, 2000 (GB) .................................. 0009853

(51) Int. Cl.
*A01N 43/04* (2006.01)
*A61K 31/70* (2006.01)
*A23L 1/10* (2006.01)

(52) U.S. Cl. ........................... 514/42; 514/43; 514/45; 514/46; 514/47; 514/48; 514/49; 514/50; 514/51; 426/1; 426/805; 424/84

(58) Field of Classification Search ................. 514/42, 514/43, 45, 49; 426/1, 805; 424/84
See application file for complete search history.

(56) References Cited

U.S. PATENT DOCUMENTS 4,758,553 A * 7/1988 Ogoshi ........................ 514/47
5,188,851 A * 2/1993 Mamoto et al. ............... 426/2
5,776,490 A   7/1998 Chu et al.

FOREIGN PATENT DOCUMENTS

WO   WO 96 11707   4/1996
WO   WO 97 40702   11/1997

OTHER PUBLICATIONS

Kubitza et al., "Identification of feed enhancers for juvinile largemouth bass *Micropterus salmoides*", Aquaculture, vol. 148, No. 2-3, 1997, pp. 191-200.*
Storebakken et al., Akvaforsk, Institute of Aquaculture Research, AS, Norway, 1998.*
Database WPI, Section Ch. Week 199538, Derwent Publications Ltd., London, GB; Cl. D13, AN 1995-287919 7, XP002158862 & JP 07 184595 A (Nippon Seishi KK), Jul. 25, 1995, abstract.
Fernando Kubitza et al., "Identification of feed enhancers for juvenile largemouth bass *Micropterus salmoides*" Aquaculture, vol. 148, No. 2-3, 1997, pp. 191-200.
Gary L. Rumsey et al., "Nutritional value of dietary nucleic acids and purine bases to rainbow trout (*Oncorhynchus mykiss*)" Aquaculture, vol. 108, No. 1-2, 1992, pp. 97-110.
Database WPI, Section Ch. Week 198209, Derwent Publications Ltd., London, GB; Cl. D13, AN 1982-16704E, XP002158863 & JP 57 012972 (Takeda Chem Ind. Ltd.), Jan. 22, 1982, abstract.
Database WPI, Section Ch. Week 198711, Derwent Publications Ltd., London, GB; Cl. B04, An 1987-076355, XP002158864 & JP 62 029530 (Nisshin Flour Milling Co), Feb. 7, 1987, abstract.

* cited by examiner

*Primary Examiner*—James O. Wilson
*Assistant Examiner*—Traviss C. McIntosh, III
(74) *Attorney, Agent, or Firm*—Drinker Biddle & Reath LLP

(57) ABSTRACT

The present invention provides for the improved uptake of feed additives, pigments for use in coloring the flesh and the like. This improved intestinal uptake of foodstuffs and additives is effected through enhancing the development of the intestinal tract. Specifically the present method comprises of feeding fish with a diet which has an augmented level of nucleotides present therein. The nucleotides may be selected from the group consisting of nucleotides of uridine, guanosine, cytidine, thymindine, adenosine and mixtures thereof. The resultant improvement in the development of the intestinal tract leads to an improvement of the intestinal surfaces to absorb nutrients and/or dietary additives, this increase being at least partly due to an increase in gut surface area, for example through an increase in villus height.

8 Claims, No Drawings

FISH FEED WITH INCREASED NUCLEOTIDE CONTENT

The present invention relates to a method of improving the development of the gut intestinal tract in fish. Specifically, by means of supplementing the normal levels of nucleotides present in the diet of the fish, improved differentiation and development of the cells of the intestinal tract occurs, this having the advantageous effect of enhancing intestinal absorbtion of feed additives and pigmentation for colouring the flesh.

It has been previously shown in the literature that dietary nucleotides are known to exert a significant influence on many mammalian immunological and physiological functions. More specifically, it is known that these nucleic acid precursors are instrumental in the healthy differentiation and development of the cells of the intestinal tract. Diets supplemented with nucleotides lead to increased intestinal mass, gut wall thickness, accelerated mucosal repair after infection or diarrhoea and enhanced populations of gut micro flora. In mammalian species, it has been demonstrated that additional dietary nucleotides induce an increase in the height of the intestinal villi resulting in an overall expansion of the total mucosal surface area. These studies have, so far, been confined to mammalian species.

It is an object of the present invention to provide a method of enhancing the development of the intestinal tract in fish.

A further object of the present invention is to provide a method of facilitating an increase in the intestinal uptake of foodstuffs and additives.

According to the present invention there is provided a method of improving the development of the intestinal tract in fish, the method comprising augmenting the levels of nucleotides present in the diet of fish.

By "development of the intestinal tract" it is meant that the ability of the intestinal surfaces to absorb nutrients and/or dietary additives is increased. Generally, this increase in absorbtion is at least in part due to an increase in gut surface area, for example by an increase in villus height.

Advantageously, the nucleotides may be selected from the group consisting of nucleotides of uridine, guanosine, cytidine, thymidine, adenosine and mixtures thereof.

The present invention encompasses the use of any nucleotide and the nucleotides may be comprised either of a single nucleotide type or as a mixture in combination with other nucleotide types.

It should be noted that modified (eg methylated), synthetically derived mimetics or functionally equivalent molecules of nucleotides of uridine, guanosine, cytidine, thymidine and adenosine may be used in the present invention.

Preferably the dietary nucleotide level is augmented by means of providing either a dietary composition comprising high levels of nucleotides or by providing a feed in which nucleotide levels have been deliberately augmented.

In one embodiment, the present invention provides a dietary composition of the feed, which contains at least 0.01% of nucleotides and preferably at least 0.02% of nucleotides, relative to the total weight of the diet.

Surprisingly it has been found that the increased nucleotide dietary concentration leads to enhanced levels of absorbtion of dietary pigment, consequently we have observed a change in flesh colour of the fish fed nucleotide enhanced diets in combination with dietary pigments.

The invention also provides the use of nucleotides to enhance uptake of pigment by fish.

Accordingly, the present invention also provides a method of modifying fish flesh colour, said method comprising the dietary administration of nucleotides and pigment.

It is anticipated that the uptake of non-pigment dietary additives will likewise be enhanced. Dietary additives in question include medicaments such as antibiotics, vaccines, vitamins, and the like. Thus, the present invention provides a method of enhancing the intestinal uptake of such additives in fish by enhancing the nucleotide content of the diet.

In a further aspect, the present invention provides a dietary composition comprising nucleotide and pigment or other dietary additives. Suitable pigments include astaxanthin, and in one preferred embodiment the dietary composition comprises astaxanthin and 0.028% by weight nucleotides.

Our research has been conducted using dietary supplements with high levels (about 14%) of the nucleotides. Diets would already contain levels of endogenous nucleotides, but a supplement added at 0.2% would add about a further 0.03% of nucleotides.

Research has shown that supplementation for feeds induces similar changes in the morphology of the piscine intestinal tract to those found in other animals. Trials in fish of various weights ranging from below 40 g to 2,000 g indicated that the villus heights in the distal intestines of these fish were increased by up to 21.5%.

Further experimentation investigating and quantifying the effects of the introduction of increased nucleotides into fish by means of inclusion in dietary intake are outlined below, in the following, non-limiting example.

EXAMPLE 1

Fish of about 200 g were fed a diet containing about 0.2% of the supplement which contained about 14% nucleotides (diets therefore contained about 0.028% added nucleotides) for 3 weeks. At the end of this period villus height in the distal region of the gut were about 21% greater than in the fish fed control diets. Several similar trials have been carried out in different sizes of fish; in all cases similar results were achieved.

Further to the finding that villus height was increased by the addition of supplementary levels of nucleotides, an additional effect of the in feed nucleotide was revealed by experimentation. It has been observed that fish fed a nucleotide supplemented diet exhibited a greater pigment coloration in their flesh. It is hypothesised that the increased gut surface area which resulted due to the initial addition of the nucleotides in the diet, enhanced absorbtion of dietary pigment into the blood which in turn led to improved deposition of pigment in the muscle. This enhanced deposition effect may allow a reduction in the dietary pigment concentration for the desired flesh coloration of consequential implications for raw material costs.

EXAMPLE 2

Fish of initial weight of about 100 g were fed on diets including 0.2% of the supplement containing about 14% nucleotides (diet contained about 0.028% of nucleotides) for 17 weeks. Treated fish showed pigment (astaxanthin) levels of 9% or greater than seen in the control experiments.

It can be concluded that, due to the physiological effect induced by the addition of nucleotides to the diet and of increasing the villus size, there is a supplementary effect of enhancing the absorption and uptake of other feed additives.

At present an enhanced absorption of dietary pigment into the blood has been shown to lead to improved deposition of colouring pigment in the muscle.

This principle can be further extended to predict that the increased villus size and resultant increase in absorptive surface area of the intestine, due to increased levels of dietary nucleotides will also lead to enhanced uptake of other feed additives such as protein based additives, antigenic preparations or therapeutic substances including antibiotics.

The invention claimed is:

1. A method of improving the development of the intestinal tract in fish, the method comprising administering to said fish a diet containing augmented nucleotide levels obtained by adding nucleotides to the diet, wherein the added nucleotides comprise a mixture of nucleotides of uridine, guanosine, cytidine, thymidine, and adenosine, in an amount effective to improve the development of said fish's intestinal tract.

2. A method of modifying fish flesh colour, said method comprising the dietary administration of nucleotides and pigment to fish, wherein the nucleotides comprise a mixture of nucleotides of uridine, guanosine, cytidine, thymidine, and adenosine in combination with a pigment in an amount effective to modify said fish flesh colour.

3. The method as claimed in claim 2 wherein the method also includes the dietary administration of non-pigment dietary additives.

4. The method as claimed in claim 3 wherein the dietary additives include medicaments.

5. The method according to claim 4 wherein the medicaments are selected from the group consisting of antibiotics, vaccines and vitamins.

6. A method of enhancing the intestinal uptake of dietary additives in fish, the method comprising feeding to the fish a diet comprising an enhanced nucleotide content obtained by adding nucleotides to the diet, wherein the added nucleotides comprise a mixture of nucleotides of uridine, guanosine, cytidine, thymidine, and adenosine, in an amount effective to enhance the intestinal uptake of dietary additives.

7. A dietary composition for fish comprising nucleotides and astaxanthin, wherein the nucleotides comprise a mixture of nucleotides of uridine, guanosine, cytidine, thymidine, and adenosine.

8. The composition as claimed in claim 7 wherein the dietary composition comprises 0.028% by weight nucleotides.

* * * * *